US008579922B2

(12) United States Patent
Glick et al.

(10) Patent No.: US 8,579,922 B2
(45) Date of Patent: Nov. 12, 2013

(54) METHOD OF SUTURE IDENTIFICATION AND MESH MARKING FOR ORIENTING AND LOCATING A MESH DURING HERNIA REPAIR

(75) Inventors: Jonathan P. Glick, Hamden, CT (US); Richard Schiretz, Middletown, CT (US)

(73) Assignee: Covidien LP, Mansfield, MA (US)

( * ) Notice: Subject to any disclaimer, the term of this patent is extended or adjusted under 35 U.S.C. 154(b) by 373 days.

(21) Appl. No.: 12/889,497

(22) Filed: Sep. 24, 2010

(65) Prior Publication Data
US 2011/0082478 A1   Apr. 7, 2011

Related U.S. Application Data

(60) Provisional application No. 61/248,605, filed on Oct. 5, 2009.

(51) Int. Cl.
*A61B 17/04* (2006.01)
(52) U.S. Cl.
USPC .......................................................... 606/148
(58) Field of Classification Search
None
See application file for complete search history.

(56) References Cited

U.S. PATENT DOCUMENTS

| 5,216,700 | A | | 6/1993 | Cherian |
| 5,474,543 | A | * | 12/1995 | McKay ............................ 604/272 |
| 5,489,294 | A | * | 2/1996 | McVenes et al. ............... 607/120 |
| 5,772,593 | A | | 6/1998 | Hakamata |
| 5,961,538 | A | * | 10/1999 | Pedlick et al. .................. 606/232 |
| 6,254,635 | B1 | * | 7/2001 | Schroeder et al. ............. 623/2.13 |
| 6,322,571 | B1 | * | 11/2001 | Adams ............................ 606/151 |
| 6,736,823 | B2 | * | 5/2004 | Darois et al. ................... 606/151 |
| 7,021,316 | B2 | * | 4/2006 | Leiboff ........................... 128/898 |
| 7,101,381 | B2 | * | 9/2006 | Ford et al. ...................... 606/151 |
| 2003/0125759 | A1 | | 7/2003 | Mirizzi et al. |
| 2003/0139775 | A1 | * | 7/2003 | Grafton .......................... 606/228 |
| 2003/0187516 | A1 | | 10/2003 | Amid et al. |
| 2003/0192561 | A1 | | 10/2003 | Murphy et al. |
| 2004/0019360 | A1 | | 1/2004 | Farnsworth et al. |
| 2004/0039453 | A1 | | 2/2004 | Anderson et al. |
| 2005/0288691 | A1 | | 12/2005 | Leiboff |

(Continued)

FOREIGN PATENT DOCUMENTS

| EP | 1836970 A1 | 9/2007 |
| WO | WO 02/07648 A1 | 1/2002 |
| WO | WO 2007/094002 A2 | 8/2007 |
| WO | WO 2010/026357 A1 | 3/2010 |

OTHER PUBLICATIONS

European Search Report for EP 10251733.1-1269 date of completion is Jan. 11, 2011 (3 pages).
European Search Report for EP 12 18 0079 dated Dec. 4, 2012.

*Primary Examiner* — Corrine M McDermott
*Assistant Examiner* — Son Dang

(57) ABSTRACT

A suture kit includes a plurality of flexible strands of suture, each of the strands of suture having one or more suture markings indicative of a suture orientation and a mesh material configured to enable the strands of suture to be passed therethrough, wherein at least one quadrant/section of the mesh material having one or more mesh markings indicative of a mesh material orientation. The one or more suture markings include visual indicators and the one or more mesh markings include visual indicators, the suture visual indicators corresponding to the mesh visual indicators for indicating correct orientation of the mesh material with respect to tissue of a subject.

18 Claims, 8 Drawing Sheets

(56) References Cited

U.S. PATENT DOCUMENTS

| | | |
|---|---|---|
| 2006/0224148 A1 | 10/2006 | Cho et al. |
| 2007/0110999 A1* | 5/2007 | Shalaby et al. ............... 428/364 |
| 2007/0123915 A1 | 5/2007 | Kammerer et al. |
| 2007/0167701 A1 | 7/2007 | Sherman |
| 2008/0172073 A1* | 7/2008 | Boyden et al. ................ 606/155 |
| 2009/0177077 A1 | 7/2009 | Piferi et al. |
| 2010/0094116 A1 | 4/2010 | Silverstein |
| 2011/0184441 A1* | 7/2011 | St-Germain ................... 606/151 |
| 2013/0158572 A1* | 6/2013 | Meneghin et al. ............ 606/151 |

* cited by examiner

METHOD OF SUTURE IDENTIFICATION AND MESH MARKING FOR ORIENTING AND LOCATING A MESH DURING HERNIA REPAIR

CROSS REFERENCE TO RELATED APPLICATION

The present application claims the benefit of and priority to U.S. Provisional Application Ser. No. 61/248,605 filed on Oct. 5, 2009, the entire contents of which are incorporated herein by reference.

BACKGROUND

1. Technical Field

The present disclosure relates to mesh and suture kits. Particularly, the present disclosure relates to sutures and mesh material each having one or more markings for identifying the orientation of the mesh relative to tissue of a subject.

2. Description of Related Art

It is well known that suture material is commonly used to repair openings in skin, internal organs, blood vessels, and a variety of other tissues of the human body. Conventionally, suturing of human tissue occurs during open surgery or minimally invasive surgical procedures.

In certain minimally invasive surgical procedures, e.g., endoscopic and laparoscopic surgeries, a surgeon performs diagnostic and therapeutic procedures at the surgical site through a natural body aperture or through one or more small incisions, using instruments specially designed for this purpose. Problems encountered by a surgeon in such minimally invasive surgical procedures include identifying which suture strands belong in a pair and which belong to a specific corner of a mesh material. Thus, suturing procedures can be particularly challenging in minimally invasive surgical procedures. For example, it can be difficult for a surgeon to determine various properties of the suture material being used, such as the orientation of the mesh and the distinction between the various sutures.

Additionally, complex or extensive surgical repairs may require the use of several suture anchors and up to several times as many free suture ends. In these procedures, tracking of individual suture strands and their relationship to one another, that is, suture management, can present particular challenges for a surgeon, particularly since such procedures are often arthroscopically performed using remote visualization. The surgeon must be able to identify which suture ends are associated with each suture anchor and with each other, to properly execute a repair and to ensure that a suture is not accidentally demounted from an anchor. In arthroscopic repair procedures, suture management can be particularly difficult because the visibility of the anchors at the surgical site, and of the sutures associated with the anchors, may be very limited. Moreover, the presence of a large number of suture strands extending from a surgical site can result in physical and visual clutter, further increasing the difficulty of the surgical procedure for the surgeon, and presenting a risk of tangling sutures.

Accordingly, a need exists for an improved suture kit that provides enhanced ease of use and easy identification for managing sutures, particularly in minimally invasive surgical procedures, such as procedures related to hernia repairs.

SUMMARY

The present disclosure is directed to a suture kit including a plurality of flexible strands of suture, each of the strands of suture having one or more suture markings indicative of a suture orientation and a mesh material configured to enable the strands of suture to be passed therethrough, wherein at least one quadrant/section of the mesh material having one or more mesh markings is indicative of a mesh material orientation. The one or more suture markings include visual indicators and the one or more mesh markings include visual indicators, the suture visual indicators correspond to the mesh visual indicators for indicating correct orientation of the mesh material with respect to tissue of a subject.

According to another aspect of the present disclosure, a method for suturing is disclosed, including providing a suture kit having a plurality of flexible strands of suture and a mesh material, introducing the mesh material into a surgical site, and orientating the mesh material in relation to the surgical site via one or more mesh visual indicators. The next step includes correlating the plurality of flexible strands of suture having one or more suture markings to corresponding mesh markings. Additionally, the fastening of the mesh material to the surgical site via the plurality of flexible strands is performed.

According to another aspect of the present disclosure, a surgical kit assembly is disclosed including four sutures, each of the four sutures having a different suture color and a mesh layer having four patches, each of the four patches having a different patch color. The suture colors on the sutures correspond to the patch colors on the mesh layer, the mesh layer further including lettering and a bull's eye stamp on the anterior surface of the mesh layer to indicate an orientation of the mesh layer.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF EMBODIMENTS

Figure 1:
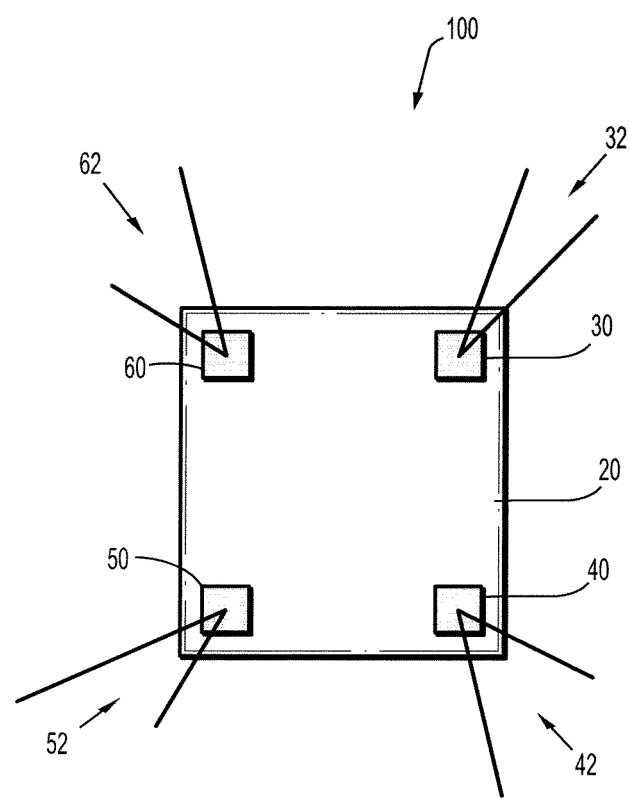
FIG. 1 is a perspective view of a plurality of different colored sutures in cooperation with a pre-marked mesh, in accordance with the present disclosure.

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The present disclosure generally provides a suture material that includes a flexible strand of suture that can have formed thereon at least one marking. The marking is adapted to provide various informational properties of the suture to a user of the improved suture material. For example, a marking can indicate information relating to at least one use characteristic of the suture. An example of a use characteristic may include orientation of the suture. Additionally, correct orientation of the mesh may also be provided by the exemplary embodiments of the present disclosure.

The present disclosure further provides suture anchor assemblies, methods and devices for anchoring suture to, for example, tissue of a subject. The assemblies, methods and devices of the present disclosure provide for the management of suture routing, positioning and identification during surgical procedures, with particular application to procedures that include tissue of a subject by using one or more suture anchors having one or more suture elements mounted thereto. The present disclosure also has particular application to arthroscopic surgery, although there is utility in other surgical procedures as well, such as open procedures.

Particular embodiments of the present disclosure will be described herein with reference to the accompanying drawings.

Referring now to the drawings, in which like reference numerals identify identical or substantially similar parts throughout the several views, FIGS. 1-7 generally describe sutures and mesh material that may be incorporated within a suture kit provided to a surgeon.

With reference to FIG. 1, a perspective view of a plurality of different colored sutures in cooperation with a pre-marked mesh, in accordance with the present disclosure is illustrated.

The suture/mesh configuration 100 of FIG. 1 includes a mesh 20, a first patch 30 having sutures 32, a second patch 40 having sutures 42, a third patch 50 having sutures 52, and a fourth patch 60 having sutures 62.

The sutures 32, 42, 52, 62 are visually coded to uniquely identify each suture element. The patches 30, 40, 50, 60 are also visually coded to uniquely identify each patch element. The visual code is preferably a color code. However, one skilled in the art can envision several different visual codes to discern the patches 30, 40, 50, 60 and the sutures 32, 42, 52, 62. Such visual codes may include using different suture materials, patterns, designs, shapes, sizes, etc. In one embodiment, a suture kit is provided incorporating at least the mesh 20, the sutures 32, 42, 52, 62, and the patches 30, 40, 50, 60. The suture kit may include at least four contrasting suture colors to aid in the ease of identifying the sutures 32, 42, 52, 62 used to secure the corners of the mesh 20 during, for example, a hernia repair procedure. Each color is assigned to a single suture.

The first patch 30 provides a visual indicator of the position of the first end of the first suture 32, a visual code to distinguish the first suture 32 from the other sutures 42, 52, 62, and a surface for convenient grasping by the surgeon using forceps or another surgical tool, for manipulating the first suture 32. Similarly, sutures 42, 52, 62 provide visual indicators for distinguishing such sutures from each other.

Multiple patches 30, 40, 50, 60 may be mounted on the mesh 20. Any kind of visual code compatible with use in a surgical field can be used, including a color code, a visual pattern displayed on the patches 30, 40, 50, 60, or incorporated into the shape of the patches 30, 40, 50, 60. Suture markings for visual coding can incorporate colored wax, markers, tags, or other means. For example, a color coding, shape or other identifying characteristics of the patches 30, 40, 50, 60 can match a color coding, shape or other identifying characteristic on the sutures 32, 42, 52, 62. The patches 30, 40, 50, 60 are sized for visibility and for convenience of grasping during the surgical procedure. In one embodiment, the patches 30, 40, 50, 60 have a maximum area or length of about 10 mm. However, one skilled in the art can envision manufacturing a plurality of patches having a plurality of dimensions. Additionally, the patches 30, 40, 50, 60 need not be of equal size. In other words, the first patch 30 and the second patch 40 may be 10 mm in length and the third patch 50 and the fourth patch 60 may be 1 inch in length, depending on desired applications.

In another embodiment, the patches 30, 40, 50, 60 may include an aperture for engagement by a hook, a surgical grasper, or for passing another suture element therethrough. If desired, tactile elements may be formed into or mounted to the patches 30, 40, 50, 60. In addition, at least one patch can optionally have one or more holes formed therein, such that suture elements are able to pass therethrough. In other words, a plurality of patches may be incorporated within each corner of the mesh 20. Of course, the patches 30, 40, 50, 60 need not only be located on the corners of the mesh 20. The patches 30, 40, 50, 60 may be positioned on any location of the mesh 20.

The sutures 32, 42, 52, 62 may be coated with wax (beeswax, petroleum wax, polyethylene wax, or others), silicone (DOW CORNING® silicone fluid 202A or others), silicone rubbers (NUSIL TECHNOLOGY™ Med 2245 and Med 2174 with a bonding catalyst, or others) PTFE (TEFLON®, HOSTAFLON®, or others), PBA (polybutylate acid), ethyl cellulose (FILODEL™) or other coatings, to improve lubricity of the braid, knot security, or abrasion resistance, for example.

The sutures 32, 42, 52, 62 may be any combination of natural (clear), white, blue, green, violet, black, or any other non-flesh color to aid in contrast and identification. Also, the sutures 32, 42, 52, 62 may be configured as monofilament, multifilament, braid, barbed, and/or any combination thereof. Moreover, the sutures 32, 42, 52, 62 may consist of absorbable, non-absorbable monomers, polymers, and combinations thereof.

The mesh 20 may also be marked in four or more regions, such as with four patches 30, 40, 50, 60 corresponding to colors that match the sutures 32, 42, 52, 62. Thus, the one or more suture markings may be suture color markings and the one or more mesh markings may be mesh color markings, the suture color markings corresponding to the mesh color markings for indicating correct orientation of the mesh material with respect to tissue of a subject. In other words, each colored suture 32, 42, 52, 62 may correspond to a patch 30, 40, 50, 60 on the mesh 20 having the same color for aiding the surgeon in identifying which suture should be matched with which patch of the mesh 20.

The color markings of the mesh 20 may be derived by either incorporating dyed yarns in a mesh weave or by a stamping process after the mesh 20 is woven. The patches 30, 40, 50, 60 may be of any desirable size. They may be small enough to cover a minor portion of the corner of the mesh 20 or they may be large enough to encompass an entire quadrant of the mesh 20. The mesh 20 may also be provided in a plurality of shapes and sizes (see FIG. 7). For example, the mesh 20 may be square, rectangular, circular, oval or other shapes typical for repairs where the mesh 20 is utilized.

In use, the sutures 32, 42, 52, 62 are passed through tissue that is being sutured, and a user is able to discern at least one use characteristic (e.g., orientation) of the suture based on the indications provided by at least one marking that is formed on the suture. The marked sutures 32, 42, 52, 62 are advantageous in that they provide an enhanced ease of use of the sutures 32, 42, 52, 62 by a surgeon, and facilitate in alleviating some of the visibility and orientation problems encountered when suturing tissue, particularly in a minimally invasive surgical procedure.

One skilled in the art will appreciate that the suture material of the present disclosure can be otherwise constructed to indicate other use characteristics of the suture material and/or to enhance visibility of the suture. For example, at least one marking formed on a flexible strand of suture as described herein can be radiopaque. Alternatively, the markings on a suture described herein can be of a contrasting color. For example, at least one marking can be of a color other than the color of the suture. Further, the markings formed on the sutures described herein can be of a texture different from a texture of the suture. For example, the markings can be indented in the strand of suture, or raised on the suture strand. In addition, a person skilled in the art will appreciate that the sutures 32, 42, 52, 62 of the present disclosure can include any combination of markings or features described herein, as well as other markings or features known in the art.

Figure 2:
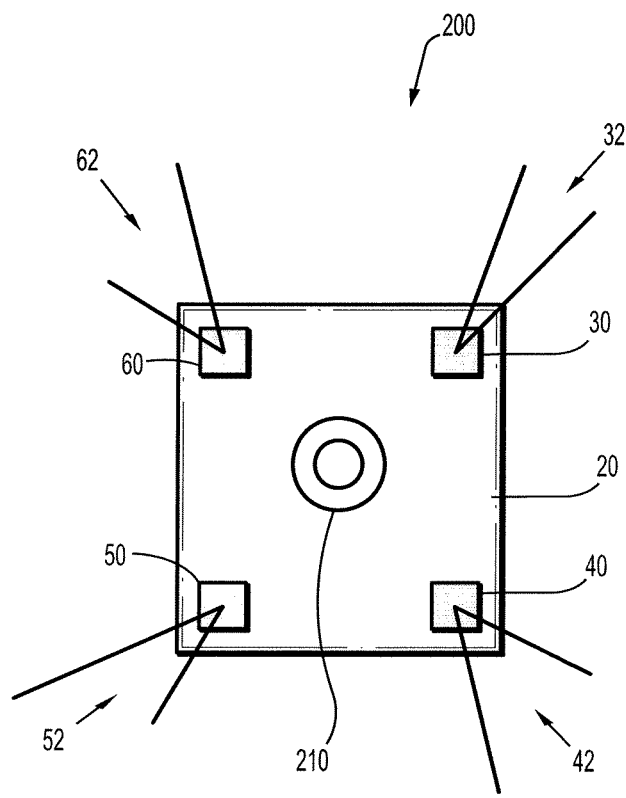
FIG. 2 is a perspective view of a plurality of different colored sutures in cooperation with a pre-marked mesh having a bull's eye stamp on the anterior side of the mesh, in accordance with the present disclosure.

With reference to FIG. 2, a perspective view of a plurality of different colored sutures in cooperation with a pre-marked mesh having a bull's eye stamp on the anterior side of the mesh, in accordance with the present disclosure is illustrated.

Like reference numerals of FIG. 1 that identify identical or substantially similar parts of FIG. 2 will not be described in this section. In FIG. 2 the suture/mesh configuration 200 further includes a bull's eye stamp 210.

The bull's eye stamp 210 may be used as an alternative to coloring the sutures 32, 42, 52, 62 or in addition to coloring the sutures 32, 42, 52, 62. It is possible to apply an adhesive to the mesh 20, to print on the mesh 20, to stamp the mesh 20 and/or to form symbols on the mesh 20. Symbols may also be introduced into the mesh 20 by means of cutouts or the like. The mesh 20, or several portions of the mesh 20 in which area the mesh structure of the object is desired to be stamped, can also be referred to as the identification surface/portion/area. Moreover, it is conceivable for the mesh 20 to serve as a support for or to receive any desired parts, not just sutures 32, 42, 52, 62.

The bull's eye stamp 210 formed on the mesh 20 is preferably formed by means of deformation, in particular as a result of pressure and/or heat. This means that the material forming the bull's eye stamp 210 is heated or compressed until a continuous surface is formed. The definition "continuous surface" does not mean that a completely smooth and homogeneous bull's eye stamp 210 structure need be present. It is acceptable if some interstices remain in the continuous surface, even if the surface is not completely continuous. The bull's eye stamp 210 formed on the mesh 20 can be sufficient to serve as a base or support for the information, symbols, writing/lettering, stickers, or other items that are to be applied or introduced. If the purpose of the bull's eye stamp 210 requires, it should be possible for an adhesive to be able to adhere sufficiently firmly to this bull's eye stamp 210.

Additionally, the bull's eye stamp 210 may be used to orient/direct the mesh 20. However, the bull's eye stamp 210 may also be used to locate and/or center and/or position the mesh 20 over one or more defects. Also, there may be a plurality of bull's eye stamps 210 in any shape or size across the entire length of the mesh 20.

Figure 3:
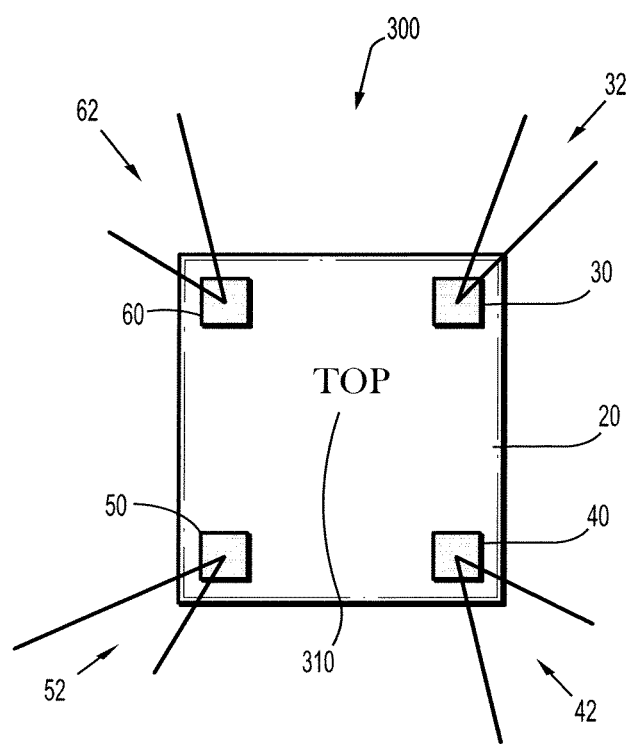
FIG. 3 is a perspective view of a plurality of different colored sutures in cooperation with a pre-marked mesh having lettering across the anterior side of the mesh, in accordance with the present disclosure.

With reference to FIG. 3, a perspective view of a plurality of different colored sutures in cooperation with a pre-marked mesh having lettering across the anterior side of the mesh, in accordance with the present disclosure is illustrated.

Like reference numerals of FIG. 1 that identify identical or substantially similar parts of FIG. 3 will not be described in this section. In FIG. 3 the suture/mesh configuration 300 further includes a lettering 310.

Additionally, lettering 310 may be placed on the surface of the mesh 20. The lettering 310 may be placed on the anterior (ventral) facing of the mesh 20. The lettering 310 may be any desired word, such as "TOP." The lettering 310 may be positioned on any portion of the mesh 20 in any size and in any color. Additionally, the lettering 310 may consist of a plurality of the same words (e.g., "TOP," "TOP," "TOP,") or different words (e.g., "TOP," "HERE," etc.) spread throughout the surface of the mesh 20. The lettering 310 may be presented in a serial manner or in a parallel manner and the words may be spaced apart in predetermined horizontal or vertical intervals.

Figure 4:
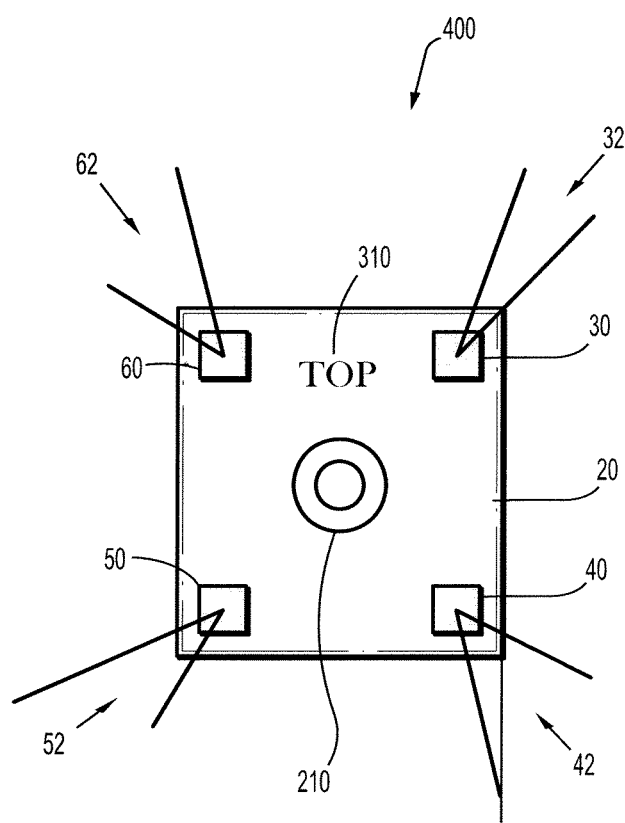
FIG. 4 is a perspective view of a plurality of different colored sutures in cooperation with a pre-marked mesh having both a bull's eye stamp and lettering across the anterior side of the mesh, in accordance with the present disclosure.

With reference to FIG. 4, a perspective view of a plurality of different colored sutures in cooperation with a pre-marked mesh having both a bull's eye stamp and lettering across the anterior side of the mesh, in accordance with the present disclosure is illustrated.

Like reference numerals of FIG. 1 that identify identical or substantially similar parts of FIG. 4 will not be described in this section. In FIG. 4 the suture/mesh configuration 400 further includes both the bull's eye stamp 210 and the lettering 310.

The advantages of having both the lettering 310 (e.g., "TOP") and the bull's eye stamp 210 stamped on the anterior side of the mesh 20 would be to assure the surgeon that the proper side of the mesh 20 is in contact with the correct type of tissue of the subject. For example, some mesh products have coatings on the posterior (dorsal) side specific to alleviate adhesion, aid in healing, and correct placement of the mesh 20. If the mesh 20 is positioned in an incorrect position (e.g., upside down or backwards), the surgeon would be able to determine that the coating is facing upward or that the lettering is backwards (see FIG. 6). Thus, a combination of different markings may be incorporated within the same mesh 20 of a suture kit.

Figure 5:
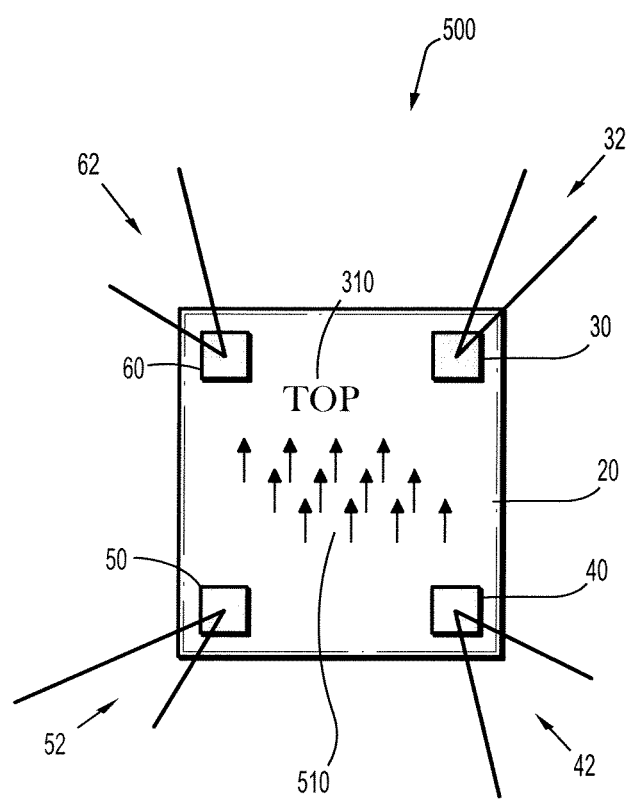
FIG. 5 is a perspective view of a plurality of different colored sutures in cooperation with a pre-marked mesh having both lettering and arrow-like indicia across the anterior side of the mesh, in accordance with the present disclosure.

With reference to FIG. 5, a perspective view of a plurality of different colored sutures in cooperation with a pre-marked mesh having both lettering and arrow-like indicia across the anterior side of the mesh, in accordance with the present disclosure is illustrated.

Like reference numerals of FIG. 1 that identify identical or substantially similar parts of FIG. 5 will not be described in this section. In FIG. 5 the suture/mesh configuration 500 further includes arrow-like indicia 510.

The arrow-like indicia 510 may be placed on a top surface of the mesh 20 or on an anterior surface of the mesh 20, either at the corners of the mesh 20 or along a length of the mesh 20 in predetermined spaced apart intervals. The arrow-like indicia 510 may preferably be placed so that they face one direction. However, one skilled in the art may envision placing a plurality of arrow-like indicia 510 in a number of configurations, where the arrows have different shapes and sizes and colors depending on the desired application. Thus, a combination of different markings may be incorporated within the same mesh 20 of a suture kit.

Figure 6:
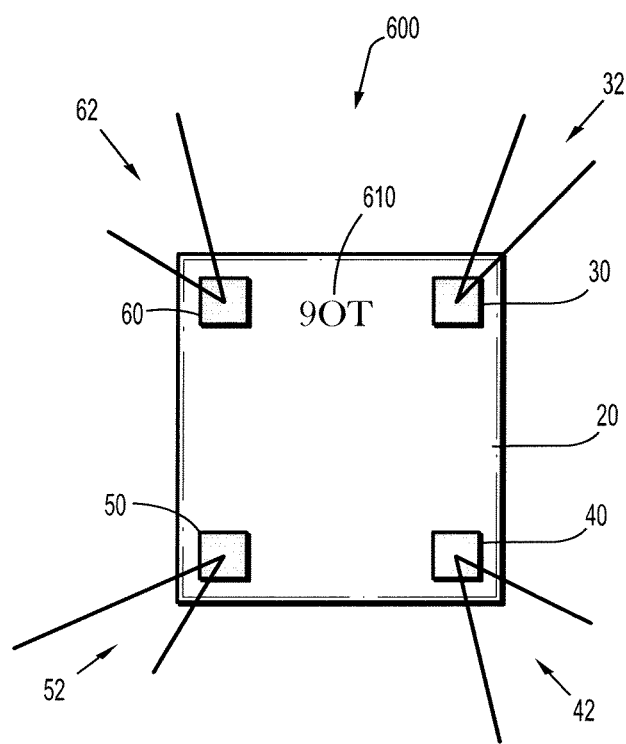
FIG. 6 is a perspective view of a plurality of different colored sutures in cooperation with a pre-marked mesh having lettering across the anterior side of the mesh, where the lettering indicates that the orientation of the mesh is incorrect, in accordance with the present disclosure.

With reference to FIG. 6, a perspective view of a plurality of different colored sutures in cooperation with a pre-marked mesh having lettering across the anterior side of the mesh, where the lettering indicates that the orientation of the mesh is incorrect, in accordance with the present disclosure is illustrated.

Like reference numerals of FIG. 1 that identify identical or substantially similar parts of FIG. 6 will not be described in this section. In FIG. 6 the suture/mesh configuration 600 further includes lettering 610.

Lettering 610 indicates to a surgeon using the mesh 20 and the sutures 32, 42, 52, 62 that the mesh 20 has been positioned backwards or upside-down. If the incorrect side of the mesh 20 is placed on the tissue site, the surgeon would see, in this example, the lettering 610 read "9OT" instead of "TOP" and would be inclined to flip the mesh 20 to correct the orientation.

Additionally, the lettering may refer to cardinal directions or cardinal points, such as "posterior," "anterior," "dorsal," and "ventral." Of course, only the initials of the cardinal directions "P," "A," "D," and "V" may be used. Moreover, any type of lettering or phrases or text or symbols in any language may be used to indicate an orientation/direction of the mesh 20.

Figure 7:
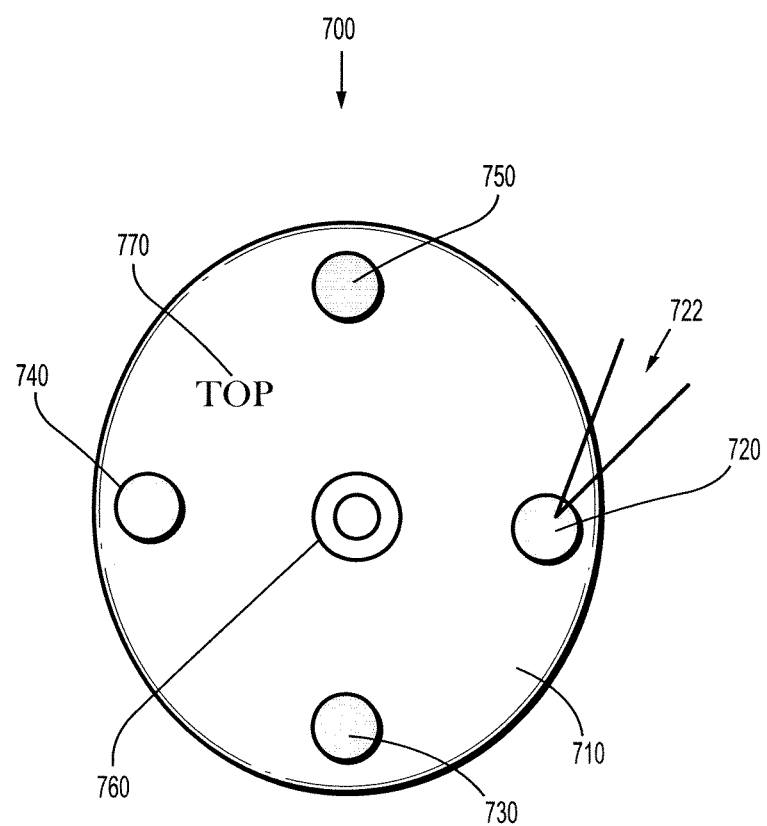
FIG. 7 is a perspective view of a plurality of different colored sutures in cooperation with a pre-marked mesh having both a bull's eye stamp and lettering across the anterior side of the mesh, where the mesh and the patches on the mesh are circular, in accordance with a second embodiment of the present disclosure.

With reference to FIG. 7, a perspective view of a plurality of different colored sutures in cooperation with a pre-marked mesh having both a bull's eye stamp and lettering across the anterior side of the mesh, where the mesh and the patches on the mesh are circular, in accordance with a second embodiment of the present disclosure is illustrated.

The suture/mesh configuration 700 includes a mesh 710, a first patch 720 having sutures 722, a second patch 730, a third patch 740, and a fourth patch 750. Each of the patches 720, 730, 740, 750 may have a plurality of sutures passed therethrough. Additionally, the mesh 710 includes a bull's eye stamp 760 and lettering 770.

The suture/mesh configuration 700 illustrates a circular mesh 710 having circular patches 720, 730, 740, 750 positioned on the outer circumference/perimeter of the mesh 710. One skilled in the art can envision a plurality of different mesh/suture configurations of a variety of different shapes, sizes, and colors being incorporated within a suture kit.

Figure 8A:
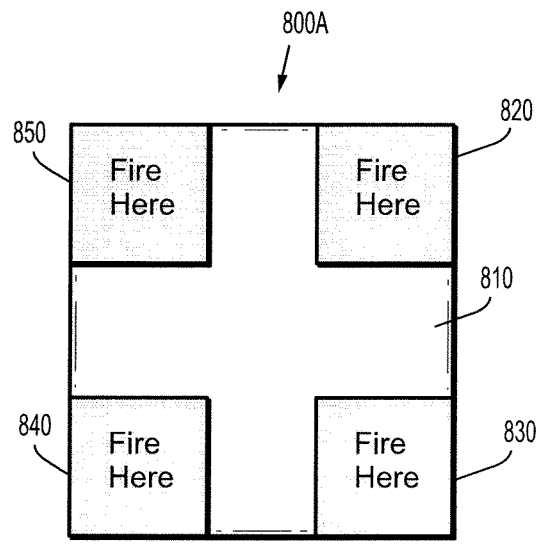
FIG. 8A is a perspective view of a pre-marked mesh including four regions suitable for inserting surgical fasteners, in accordance with a third embodiment of the present disclosure.
Figure 8B:
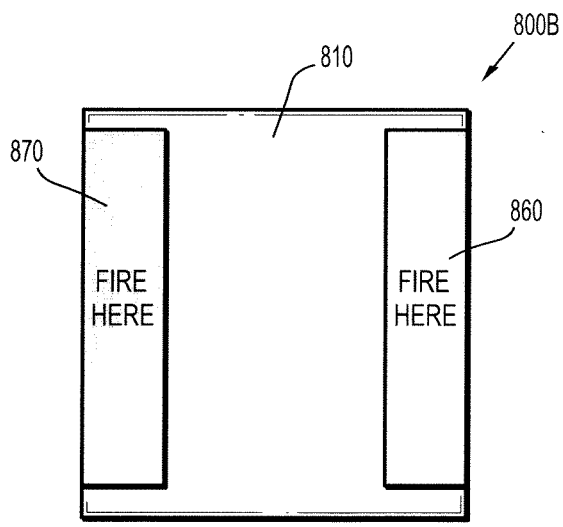
FIG. 8B is a perspective view of a pre-marked mesh including two regions suitable for inserting surgical fasteners, in accordance with a third embodiment of the present disclosure.

With reference to FIGS. 8A and 8B, a perspective view of a pre-marked mesh including a plurality of regions suitable for inserting tacks, respectively, in accordance with a third embodiment of the present disclosure is presented.

In FIG. 8A, the mesh design 800A includes a mesh 810 having four regions 820, 830, 840, 850 suitable for firing or inserting fasteners. In FIG. 8B, the mesh design 800B includes a mesh 810 having two regions 860, 870 suitable for firing or inserting fasteners. The regions 820, 830, 840, 850, 860, 870 are target zones for a medical professional to place fasteners, such as tacks, staples, clips or the like. The regions 820, 830, 840, 850, 860, 870 enable the medical professional to ensure correct or accurate positioning of the, for example, tacks in relation to the mesh 810. Thus, the mesh designs 800A and 800B provide a patch with one or more types of indicia that would help the surgeon ensure that the patch has been properly sized, shaped and positioned and would provide the surgeon with visual guides for fixing the patch to the tissue surrounding the surgical area. The regions 820, 830, 840, 850, 860, 870 may include any type of lettering, in any language, in any size to indicate to a surgeon the proper zone for fastening the mesh 810 to the tissue of a patient. In FIGS. 8A and 8B, the lettering "Fire Here" indicates where the surgeon should insert, for example, the tacks. The regions 820, 830, 840, 850, 860, 870 may be any shape or size and may be located on any portions of the mesh 810. Of course, one skilled in the art may contemplate using any type of grid configuration that would act as a visual guide for a surgeon and/or medical professional.

Additionally, the markings may also be attached to the mesh 810 by a variety of mechanical means such as sewing or weaving the markings into the mesh material. Similarly, markings such as metal threads may also be attached to the material by adhesive means, such as with bio-compatible glues. Moreover, the regions 820, 830, 840, 850, 860, 870 may be reinforced regions. In other words, regions 820, 830, 840, 850, 860, 870 may be thicker than the mesh 810 in order to accommodate tacks, clips or the like. These reinforced regions may be formed of a material having a higher tensile strength relative to the remainder of the mesh 810 in order to accommodate such tacks, clips or the like. Of course, one skilled in the art may contemplate using a plurality of the different materials of different tensile strengths to construct a mesh 810 for a desirable application.

In conclusion, the suture material of the present disclosure can be used in a variety of surgical procedures, for example, for repairing or re-attaching tissue. In an exemplary embodiment, the sutures can be used in a suturing procedure conducted during a minimally invasive surgical procedure, such as an endoscopic or laparoscopic procedure. In another exemplary embodiment, the suture material is used in the context of stitching epidermal disruptions. It will be understood, however, that the method described herein is equally applicable to connecting detached tissue in other contexts as well, such as during open and invasive surgical procedures.

The improved suture materials of the present disclosure can be formed from a variety of known materials that are suitable for use in forming suture material. Moreover, the exemplary embodiments of the present disclosure can be formed onto the suture material in a variety of processes. By way of example, the various suture markings embodying the present disclosure can be applied to the sutures described herein by an off-set printing process. The markings can also be applied to the sutures of the present disclosure by a pad printing process, which can involve obtaining an ink from a master, and subsequently transferring the impression to the suture material.

In another embodiment, a suture anchor assembly according to the present disclosure is provided as a kit including a suture anchor mounted to an insertion tool, and one or more visually coded suture element as described above, pre-mounted to the anchor. In a further embodiment, several different kits are provided, each having unique visual coding of included suture elements, thereby enabling the surgeon to take additional advantage of the suture management capabilities of the present disclosure for multi-anchor procedures.

Suture anchor assemblies and their application according to the present disclosure have many advantages. These advantages include, but are not limited to, advantages associated with ease of use for the surgeon/user and probable reductions in surgical time and skill required to perform soft tissue repairs. Using suture anchor assemblies according to the present disclosure also reduces the number of suture limbs requiring management about a surgical site, thereby reducing possible confusion and risk of tangling associated with conventional suture configurations.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the invention based on the above-described embodiments. Accordingly, the present disclosure is not to be limited by what has been particularly shown and described, except as indicated by the appended claims.

What is claimed is:

1. A suture kit, comprising:
   a plurality of flexible strands of suture, each of the strands of suture having one or more suture markings indicative of a suture orientation; and
   a mesh material configured to enable the strands of suture to be passed therethrough, wherein each quadrant/section of the mesh material includes a patch attached thereto having one or more patch markings indicative of a mesh material orientation;
   wherein the one or more suture markings include visual indicators and the one or more patch markings include visual indicators, each of the suture visual indicators configured to match corresponding patch visual indicators for enabling correct matching and indicating correct orientation of the mesh material with respect to tissue of a subject.

2. The suture kit according to claim 1, wherein each of the strands of suture pass through a corresponding patch in each quadrant/section of the mesh material.

3. The suture kit according to claim 1, wherein the visual indicators are color markings.

4. The suture kit according to claim 1, wherein the plurality of flexible strands of suture include at least four contrasting color sutures configured to match four contrasting color patch markings.

5. The suture kit according to claim 1, wherein each patch of each quadrant/section of the mesh material is a rectangle having a length less than a length of the quadrant/section.

6. The suture kit according to claim 1, wherein the visual indicators are prepared with a dye process or a stamping process.

7. The suture kit according to claim 1, wherein each of the plurality of flexible strands of suture is configured as monofilament, multifilament, barbed or combinations thereof.

8. The suture kit according to claim 1, wherein each of the plurality of flexible strands of suture includes polymers that are absorbable, non-absorbable and combinations thereof.

9. The suture kit according to claim 1, wherein the visual indicators are selected from a group consisting of a plurality of colors, shapes, patterns and/or end effectors.

10. The suture kit according to claim 1, wherein the visual indicators are derived by incorporating dyed yarns in a mesh weave of the mesh material.

11. The suture kit according to claim 1, wherein the visual indicators are derived by a stamping process after the mesh material is woven.

12. The suture kit according to claim 1, wherein the mesh material includes lettering placed on a top surface or an anterior surface of the mesh material.

13. The suture kit according to claim 12, wherein the lettering on the top surface or the anterior surface of the material is "TOP."

14. The suture kit according to claim 1, wherein the mesh material includes a bull's eye stamp placed on a top surface or an anterior surface of the mesh material.

15. The suture kit according to claim 1, wherein the mesh material includes arrow-like indicia placed on a top surface or an anterior surface of the mesh material, either at corners of the mesh material or along a length of the mesh material in predetermined spaced apart intervals.

16. The suture kit according to claim 1, wherein the patch visual indicators are of a variable size.

17. The suture kit according to claim 1, wherein the suture visual indicators and the patch visual indicators are radiopaque.

18. A surgical kit assembly, comprising:
   four sutures, each of the four sutures having a different suture color; and
   a mesh layer having four patches, each of the four patches having a different patch color;
   wherein the suture colors on the sutures are configured to match corresponding patch colors on the mesh layer to enable correct matching therebetween, the mesh layer further including at least indicia and a bull's eye stamp on the anterior surface of the mesh layer to indicate an orientation of the mesh layer.

* * * * *